United States Patent [19]

Tanabe

[11] 4,105,679

[45] Aug. 8, 1978

[54] PROCESS FOR PRODUCING A CYLIC ETHER FROM AN ACETIC ESTER OF A 1,4-GLYCOL

[75] Inventor: Yasuo Tanabe, Kurashiki, Japan

[73] Assignee: Mitsubishi Chemical Industries Ltd., Tokyo, Japan

[21] Appl. No.: 763,715

[22] Filed: Jan. 28, 1977

[30] Foreign Application Priority Data

Feb. 4, 1976 [JP] Japan .................................. 51-11077
Mar. 16, 1976 [JP] Japan .................................. 51-28451

[51] Int. Cl.² .......................................... C07D 307/08
[52] U.S. Cl. ................................................ 260/346.11
[58] Field of Search ...................... 260/346.1 R, 346.11

[56] References Cited

U.S. PATENT DOCUMENTS

| 4,005,112 | 1/1977 | Smith ............................ 260/346.1 R |
| 4,005,113 | 1/1977 | Smith ............................ 260/346.1 R |
| 4,010,171 | 3/1977 | Smith ............................ 260/346.1 R |
| 4,011,244 | 3/1977 | Smith ............................ 260/346.1 R |

FOREIGN PATENT DOCUMENTS 1,170,222  11/1969  United Kingdom ............ 260/346.1 R Primary Examiner—Richard L. Raymond
Attorney, Agent, or Firm—Bierman & Bierman

[57] ABSTRACT

A process for producing tetrahydrofuran or dihydrofuran from an acetic ester of 1,4-butanediol or 1,4-dihydroxybutene-2 is disclosed in which the raw material liquid acetic ester and steam are reacted in the presence of an acid catalyst in a plurality of reaction zones in liquid-gas countercurrent contact, a gaseous fraction containing the product cyclic ether is recycled to the preceding reaction zone while a liquid fraction containing unreacted raw material is transferred into the succeeding zone and the product cyclic ether is recovered from the gaseous fraction discharged from the first zone by distillation whereby the conversion of the acetic ester into the cyclic ether is improved.

13 Claims, 3 Drawing Figures

PROCESS FOR PRODUCING A CYLIC ETHER FROM AN ACETIC ESTER OF A 1,4-GLYCOL

BACKGROUND OF THE INVENTION

1. Field of the Invention

This invention relates to a process for producing a cyclic ether in a single step from an acetic ester of a glycol and, in more particular, to a process for producing tetrahydrofuran or dihydrofuran from an acetic ester of 1,4-butanediol or 1,4-dihydroxybutene-2.

2. Description of Prior Art

Tetrahydrofuran is useful as a solvent for polymeric materials, such as polyvinyl chloride and polyvinylidene chloride, and is produced by various processes; for example, catalytic hydrogenation of furan produced by decarbonylation of fulfural; reacting acetylene and formaldehyde to obtain butynediol, followed by hydrogenation and dehydrocyclization to produce tetrahydrofuran, and reacting diacetic ester of 1,4-butanediol with water in the presence of an acid catalyst (refer to British Patent 1,170,222).

From an extensive study of producing a cyclic ether, especially tetrahydrofuran, from an acetic ester of a 1,4-glycol, I have found that, if the raw material acetic ester is contacted with steam in stoichiometrically excess amount and in a liquid-gas countercurrent contact, the conversion of the acetic ester into a cyclic ether is improved and, at the same time, the desired product is readily recovered as a gaseous material from the reaction system.

I have also found that, since tetrahydrofuran and water form an azeotropic mixture, the use of an excess amount of water requires repeated distillation steps for recovering anhydrous tetrahydrofuran from the reaction product. On the other hand, if the amount of water is decreased, the conversion will lower to make the process uneconomical.

In order to obtain a reaction product containing the desired cyclic ether in high content without lowering the conversion and to recover a high quality cyclic ether by simple distillation procedure, I have conducted further investigation to find that a high quality cyclic ether substantially free from water is obtained by effecting the reaction in a plurality of reaction zones and recycling a part of the reaction product to a predetermined reaction zone. This invention has been accomplished on the basis of the above knowledge.

BRIEF SUMMARY OF THE INVENTION

An object of this invention is to provide a commercial process for producing a high quality cyclic ether from an acetic ester of a 1,4-glycol.

Another object is to produce a high quality cyclic ether substantially free from water by using a plurality of reaction vessels in combination with a plurality of distillation columns.

DETAILED DESCRIPTION OF THE INVENTION

Figure 1:
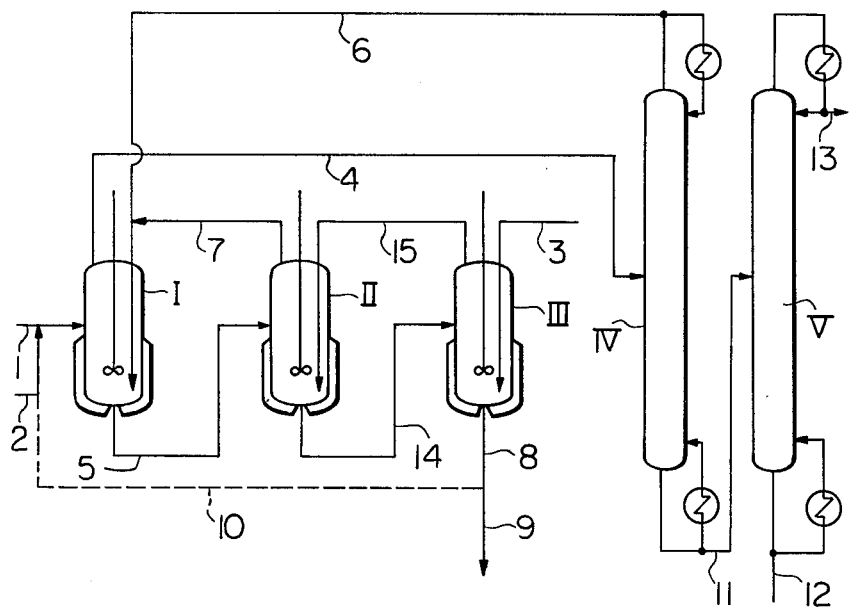
FIG. 1 illustrates a flowsheet of an apparatus suitable for carrying out the process of this invention comprising three reaction vessels and two distillation columns.

Examples of an acetic ester of 1,4-butanediol or 1,4-dihydroxybutene-2 which may be used according to this invention include, for example, mono- and di-acetic esters of 1,4-glycols, such as 1,4-diacetoxybutane, 1-hydroxy-4-acetoxybutane, 1,4-diacetoxybutene-2 and 1-hydroxy-4-acetoxybutene-2. These acetic esters may be produced by various processes. For example, butadiene, acetic acid and a molecular oxygencontaining gas are reacted in the presence of a palladium catalyst to effect acetoxylation and 1,4-diacetoxybutene-2 and 1-hydroxy-4-acetoxybutene-2 are separated from the acetoxylation product. Alternatively, the acetoxylation product is hydrogenated in the presence of a nickel- or palladium-based catalyst and 1,4-diacetoxybutane and 1-hydroxy-4-acetoxybutane are recovered from the hydrogenation product.

Such product contains mainly the abovementioned acetic esters, but, depending upon the production and purification procedures, acetic esters of 1,2- or 1,3-glycol isomer may be contained and, in some cases, butyl acetate and acetic acid which are byproducts of the hydrogenation step are also present. It is preferable to use an acetic ester of a 1,4-glycol, especially diacetic ester of 1,4-butanediol having a purity more than 99.5%.

Although 1-hydroxy-4-acetoxybutane may be produced by partial hydrolysis of 1,4-diacetoxybutane, it is preferable that allylacetate produced by reacting propylene, acetic acid and a molecular oxygen-containing gas in the presence of a palladium catalyst be subjected to OXO reaction to obtain 4-acetoxybutylaldehyde which is then converted to 1-hydroxy-4-acetoxybutane by hydrogenation; in this case the product contains 2-methyl-3-acetoxypropyl alcohol derived from 2-methyl-3-acetoxypropione aldehyde of a byproduct in the OXO reaction; however, such alcohol does not adversely affect the reaction of this invention.

The acid catalyst which may be used according to this invention should be non-volatile in nature and may be either a liquid acid and a solid acid. Examples of the liquid acid include, for example, an inorganic acid, such as sulfuric acid or phosphoric acid, and an organic sulfonic acid, such as benzene sulfonic acid, toluene sulfonic acid or trifluoromethane sulfonic acid. Among these, sulfuric acid is most preferable.

Examples of the solid acid include, for example, active clay, silica-titania, silica-alumina, silica-zirconia, chromia-alumina, silica-magnesia, natural or synthetic zeolite and a strong acid cation exchange resin.

The amount of acid catalyst to be used may vary depending upon the type employed and cannot be specified. In the case of liquid acid, an amount of from 0.01 to 100 parts by weight on the basis of one part of the raw material acetic ester is suitable. On the other hand, solid acid is often used in the form of a catalyst bed packed in a column; the amount may vary depending upon the capacity of the column and the activity of the catalyst, and is usually from 0.001 to 10 in terms of liquid hourly space velocity (LHSV, $hr^{-1}$).

According to this invention, water from any source may be used and chloride ion-free water is preferred.

According to this invention, the reaction is carried out in a plurality of reaction zones connected in series. The type and detail of such reaction zone are not critical so far as sufficient gas-liquid contact is performed, for example, a bubble column, a multi-stage bubble column, a packed bubble column, a packed column, a multi-stage packed column or a stirred tank reactor is conveniently used.

Embodiments of the mode of reaction are as follows:

(a) The reaction is conveniently carried out by using a bubble column or a stirred tank reactor containing catalyst (liquid acid or suspension bed of solid acid) and supplying to the reactor a liquid acetic ester of glycol to form a liquid phase and simultaneously water or steam, with optional external heating. A multi-stage bubble column or a packed bubble column may also be used.

(b) The reaction is carried out in a column containing packing, such as Raschig rings, bell saddles of Intalox suddles made of metal or porcelain, by supplying the raw material liquid acetic ester, non-volatile acid catalyst and steam. Though the liquid raw material and steam may be supplied downwardly from the top or upwardly from the bottom in concurrent, it is preferred that the gas and the liquid are contacted in countercurrent, preferably the liquid material being supplied downwardly and the steam upwardly. The reaction may also be carried out in a multi-stage packed column or a fixed bed of a solid acid catalyst.

In general, the apparatus is composed of a plurality of such reactors connected with one another in series. The packed column may be divided to form a plurality of reaction zones. From 2 to 10, preferably 2 to 4, tank reactors are connected in series.

It is essential that the reactor be acid resistant. When the catalyst is a solid acid which is used at a relatively low reaction temperature within the range mentioned above, the reactor is made of stainless steel SUS 316; on the other hand, when the catalyst is a liquid acid, the reaction is effected at a relatively high temperature and the reactor made of Hastelloy or glass-lined is conveniently used.

Referring to FIG. 1, I, II and III represent first, second and third reactors each equipped with a stirrer and a heating jacket, and IV and V represent first and second distillation columns.

The raw material acetic ester is supplied via pipe line 1 to the first reactor I and a liquid acid catalyst, for example, sulfuric acid is supplied via pipe line 2 optionally together with the liquid fraction recirculated via pipe line 10 from the last reactor III. Fresh water, preferably in the form of steam, is supplied via pipe line 3 to the last reactor III.

Supplied to the first reactor I are the gaseous mixture of cyclic ether, water and acetic acid discharged from the second reactor II via pipe line 7 and the gaseous top fraction containing cyclic ether and water discharged from the first distillation column IV via pipe line 6. From the top of the first reactor, a gaseous mixture of cyclic ether, water and acetic acid is discharged and it is supplied via pipe line 4 to the first distillation column IV.

From the bottom of the first reactor, a liquid fraction containing unreacted raw material, acid catalyst and acetic acid is discharged, and it is supplied via pipe line 5 to the second reactor II to which the gaseous mixture of cyclic ether, water and acetic acid discharged from the last reactor III is supplied via pipe line 15. From the bottom of the second reactor, a liquid fraction is discharged, and it is supplied via pipe line 14 to the third reactor III.

From the bottom of the third reactor, a balanced amount of a liquid fraction containing mainly the catalyst and acetic acid is discharged via pipe lines 8 and 9 and, if desired, a part of this fraction may be recycled via pipe line 10 to the first reactor.

Conditions under which the reaction in each of the reaction zones is carried out may vary depending upon the type of catalyst employed and the composition of the reaction mixture. Where a liquid acid catalyst is used, the temperature is generally from 100° to 200° C, preferably 110° to 180° C and more preferably 120° to 160° C, and the pressure is generally from atmospheric to 10 kg/cm$^2$G, preferably atmospheric to 3 kg/cm$^2$G and more preferably atmospheric to 1 kg/cm$^2$G. The reaction temperature of each succeeding reaction zone is maintained higher than that of the preceding zone and the temperature of the last zone is maintained at from 120 to 200° C, preferably 140 to 180° C.

In the case where a solid acid catalyst is used, the reaction temperature is higher than that of a liquid acid catalyst, and is usually a temperature of above 120° C.

Figure 2:
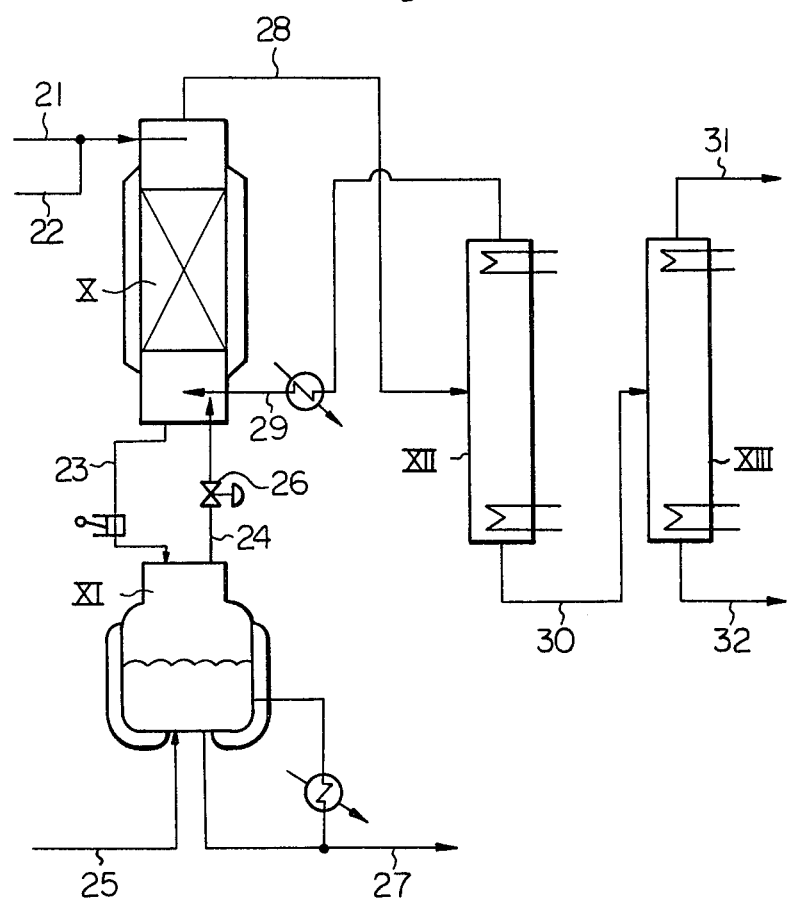
FIG. 2 illustrates a flowsheet of another apparatus comprising two reaction vessels of a packed column type and a reaction tank type, respectively, and two distillation columns.

Instead of the plurality of stirred tank reactors illustrated in FIG. 1, a combination of at least one packed column and at least one tank reactor may conveniently be used as shown in FIG. 2.

Figure 3:
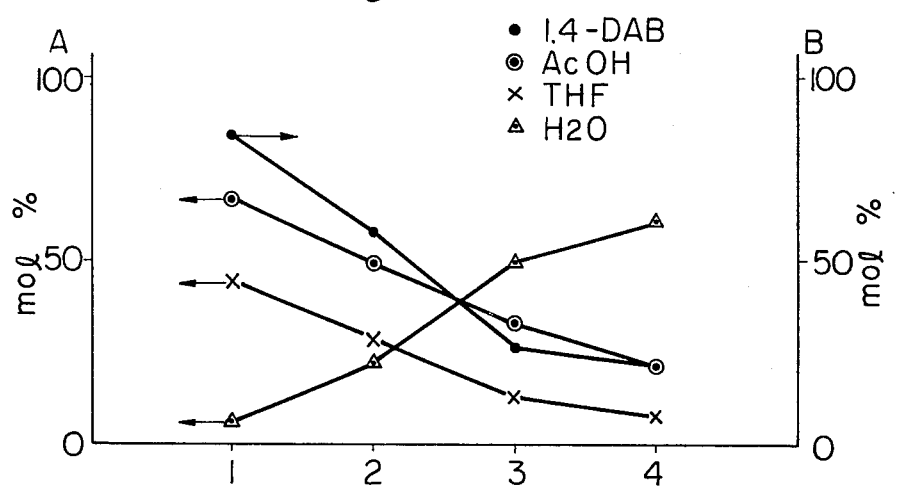
FIG. 3 is a graph showing the compositions of the gas effluent and liquid effluent discharged from each of the reaction zones, in which A and B axes represent the compositions, in terms of mole %, of the gas effluent and the liquid effluent, respectively, and the horizontal axis represents the number of reaction stages.

The composition of the gaseous effluent and the proportion of the acetic ester present in the liquid fraction from each reaction zone will vary depending upon the reaction conditions. One example in which the reaction is carried out in four reaction zones and at 140° C in the last zone is given in FIG. 3 in which abbreviations 1,4-DAP, AcOH and THF represent 1,4-diacetoxybutane, acetic acid and tetrahydrofuran, respectively.

The gaseous mixture of cyclic ether, water and acetic acid discharged from the first reactor I is supplied via pipe line 4 to the first distillation column to effect distillation, and a top fraction containing cyclic ether and water is recycled via pipe line 6 to the first reactor I; if desired, the top fraction may be recycled to any of the other reaction zones or may be divided out and recycled to each of the reaction zones. The bottom residue containing cyclic ether and acetic acid substantially free from water is supplied via pipe line 11 to the second distillation column V. From the top of the second column, the cyclic ether product having commercially required purity is obtained via pipe line 13, while the bottom residue containing acetic acid and high boiling materials is removed via pipe line 12.

The type of distillation column employed in this invention is not critical and any conventional distillation column may conveniently be used, for example, a multi-stage distillation column or a packed distillation column made of stainless steel SUS 316. The distillation may be operated under conditions such as, for example, the number of theoretical plates of from 5 to 20, under a pressure of atmospheric to 3 Kg/cm$^2$G and at a reflux ratio of 0.5 to 10.

If desired, the first stage distillation may be effected in two columns. In such case, acetic acid is separated as a bottom residue in the first column, while a mixture of cyclic ether and water is distilled out and transferred into the second column wherein a gaseous mixture of cyclic ether and water is distilled out and recycled to a predetermined reaction zone. The bottom residue containing cyclic ether of the second column is supplied to the succeeding distillation stage. The pressure of the second column is maintained higher by 2 to 15 Kg/cm²G than that of the first column.

Referring to FIG. 2, numerical figures X and XI represent first and second reactors and XII and XIII represent first and second distillation columns, respectively. In this embodiment, the first reactor is a packed column and the second reactor is of a tank type.

Supplied to the top of the first reaction column X are raw materials of the acetic ester via pipe line 21 and a liquid acid catalyst via pipe line 22, while the gaseous mixtures containing cyclic ether and water recycled from first distillation column XII via pipe line 29 and recycled from second reactor XI via pipe line 24 are supplied to the bottom. A liquid fraction containing unreacted acetic ester, acid catalyst, partial hydrolysis product, acetic acid and cyclic ether is discharged from the first reactor and is transferred via pipe line 23 into the second reactor XI to which water is supplied via pipe line 25. From the second reactor, a gaseous fraction containing cyclic ether and water is discharged, and it is supplied via pipe line 24 to the first reactor, after the gas pressure is adjusted by a control valve 26, while a liquid boiling materials and acid catalyst is removed from the bottom via pipe line 27.

A gaseous fraction containing mainly the cyclic ether is discharged from the top of the first reactor and supplied via pipe line 28 to the first distillation column XII which may be of any conventional type, for example, a multi-stage distillation column and a packed distillation column, made of, for example, stainless steel SUS 316.

The distillation in the first column is carried out under the conditions of the number of theoretical plates of from 5 to 20, under a pressure of from atmospheric to 3 Kg/cm²G and at a reflux ratio of from 0.5 to 10.

In the first column, a top fraction containing cyclic ether and water and a bottom residue of cyclic ether containing acetic acid and substantially free from water are separated, the former being recycled via pipe line 29 to the first reactor and the latter being supplied via pipe line 30 to the second distillation column XIII.

From the top of the second column, a gaseous cyclic ether having required purity is recovered via pipe line 31, while a bottom residue containing acetic acid and high boiling materials is removed via pipe line 32.

In this embodiment, the first distillation stage may be effected in two distillation columns whereby the acetic acid fraction is firstly separated as a bottom residue of the first column.

According to this invention, the reaction is effected in a plurality of reaction zones, while the gaseous product of each zone is recycled to the preceding zone and the liquid product is transferred into the succeeding zone. Thus, from the first reaction zone a cyclic ether-rich gaseous fraction (in other words, of less water content) can be obtained and a cyclic ether fraction substantially free from water can readily be recovered by simple distillation operation. Further, as the reaction mixture proceeds toward the last reaction stage, the proportion of water to the raw material acetic ester increases, thus, although the concentration of the acetic ester lowers toward the last stage, the conversion does not decrease. Meanwhile, the cyclic ether produced in the later stage is, in turn, recycled to the earlier reaction stage; then, all of the desired product of cyclic ether is recovered from the first stage in high yield.

This invention will be explained in detail by means of examples. However, it should be understood that this invention is in no way limited by these examples.

EXAMPLE 1:

The reaction was carried out using the apparatus shown in FIG. 1.

Each of the reactors I, II and III was a 50l glass-lined tank type reaction vessel equipped with a stirrer and a heating jacket through which superheated steam at 140° C was passed. Via pipe line 1, 3.58 Kg/hr of liquid 1,4-diacetoxybutane, via pipe line 2, 0.2 Kg/hr of sulfuric acid, and via pipe line 10, 2.84 Kg/hr of the liquid fraction recycled from the third reactor III were supplied to the first reactor I maintained at a temperature of 140° C under atmospheric pressure, and, at the same time, via pipe line 7, 3.23 Kg/hr of the gaseous mixture of tetrahydrofuran, steam and acetic acid discharged from the second reactor II and via pipe line 6, the gaseous azeotropic mixture of tetrahydrofuran and water discharged from the first distillation column IV were also supplied. The gaseous mixture of tetrahydrofuran, water and acetic acid discharged from the first reactor I was supplied via pipe line 4 to the first distillation column at a rate of 4.36 Kg/hr. The bottom residue of the first reactor I was supplied via pipe line 5 to the second reactor II to which the gaseous mixture of tetrahydrofuran, acetic acid and water discharged from the third reactor III was supplied via pipe line 15. The bottom residue of the second reactor II was supplied via pipe line 14 to the third reactor III to which fresh steam was supplied via pipe line 3 at a rate of 0.36 Kg/hr under atmospheric pressure. The bottom residue containing mainly unreacted acetic ester and sulfuric acid catalyst (the concentration of $H_2SO_4$ being 62% by weight) was discharged via pipe line 8 at a rate of 3.2 Kg/hr, of which 2.84 Kg/hr was recycled via pipe line 10 to the first reactor, the balance being removed via pipe line 9.

Each of the distillation columns IV and V was made of stainless steel SUS 316, had an internal diameter of 100 mm and a length of 10 m and was packed with Dickson packings.

The gaseous fraction discharged from the first reactor was supplied via pipe line 4 to the first distillation column at 5 m below the top, operated at a bottom temperature of 100° C under atmospheric pressure and at a reflux ratio of 2.0. The azeotropic top fraction of tetrahydrofuran and water discharged from the first column at a rate of 0.53 Kg/hr was recycled via pipe line 6 to the first reactor, if desired, it may be passed through an evaporator (not shown) in order to vaporise any condensed portion. The bottom residue (the water content being less than 0.01% by weight) was supplied at a rate of 3.82 Kg/hr via pipe line 11 to the second distillation column V at 5 m below the top, operated at a bottom temperature of 120° C, under atmospheric pressure and at a reflux ratio of 2.0. In the second column, tetrahydrofuran and acetic acid were separated, the former being recovered from the top via pipe line 13 at a rate of 1.41 Kg/hr and the latter being recovered from the bottom via pipe line 12 at a rate of 2.41 Kg/hr. The product tetrahydrofuran recovered had a purity of 99.9% and the yield thereof was 99.2% of the theoretical value on the basis of the 1,4-diacetoxybutane supplied.

EXAMPLE 2:

The reaction was carried out using the apparatus illustrated in FIG. 2.

First reactor X was a vertical tube made of Hastelloy having an internal diameter of 100 mm and a length of 5.5 m, equipped with a heating jacket and packed with 40l of porcelain balls (diameter being 5 mm).

Via pipe line 21, 17.4 Kg/hr of liquid 1,4-diacetoxybutane and via pipe line 22, 0.98 Kg/hr of sulfuric acid were supplied at 140° C to the top of the first reactor X, while superheated steam at 140° C was passed through the jacket. Supplied to the bottom of the first reactor were the distillate from the first distillation column XII via pipe line 29 at a temperature of 140° C, under atmospheric pressure and at a rate of 2.59 Kg/hr, after being treated in an evaporator, and the gaseous mixture discharged from second reactor XI via pipe line 24 at a temperature of 140° C and at a rate of 5.12 Kg/hr, after being regulated to atmospheric pressure.

From the top of the first reactor, a gaseous mixture of tetrahydrofuran, water and acetic acid was discharged at a rate of 13.65 Kg/hr, and it is supplied via pipe line 28 to the first distillation column XII, while a liquid fraction containing mainly unreacted 1,4-diacetoxybutane was discharged from the bottom via pipe line 23 at a rate of 12.45 Kg/hr and pumped to the second reactor XI. The second reactor was of a 100l glass-lined tank type, had an internal diameter of 500 mm, was equipped with a heating jacket, and was connected with a reboiler (not shown) made of Hastelloy.

Water was supplied at a rate of 1.95 Kg/hr via pipe line 25 to the bottom of the second reactor, which was maintained an internal pressure at a constant level of 7 Kg/cm$^2$G by adjusting the flow rate of an azeotropic mixture of tetrahydrofuran and water by means of a control valve, while the temperature was maintained at 140° C by passing heating steam through the jacket and the reboiler. Then, an azeotropic mixture of tetrahydrofuran and water containing acetic acid was discharged via pipe line 24 at a rate of 5.12 Kg/hr and supplied to the first reactor at 140° C under atmospheric pressure.

The bottom residue containing water, acetic acid, sulfuric acid, high boiling materials and small amounts of 1,4-diacetoxybutane, 1-hydroxy-4-acetoxybutane and 1,4-butanediol was removed via pipe line 27 at a rate of 9.26 Kg/hr, of which 7.61 Kg/hr was the acetic acid.

Each of the distillation columns was made of stainless steel SUS 316, had an internal diameter of 100 mm and a length of 10 m, was packed with Dickson packings and was operated under atmospheric pressure and at a reflux ratio of 2.0.

The gaseous mixture discharged from the first reactor was introduced via pipe line 28 into the first distillation column XII at 5 m below the top. A top fraction containing 81.9 mol % of tetrahydrofuran (the balance being water) was discharged at a rate of 2.59 Kg/hr and recycled to the first reactor via pipe line 29, and, at the same time, the bottom residue was discharged at a rate of 11.05 Kg/hr and introduced via pipe line 30 into the second distillation column XIII. From the second column, the product tetrahydrofuran as top fraction having a purity of more than 99.95% was recovered via pipe line 31 at a rate of 6.9 Kg/hr, and the acetic acid as bottom residue was removed via pipe line 32 at a rate of 4.15 Kg/hr.

The yield of the product tetrahydrofuran was 95.9% of the theoretical value on the basis of the 1,4-diacetoxybutane supplied.

What is claimed is:

1. A process for producing a cyclic ether by reacting an acetic ester of 1,4-butanediol or 1,4-dihydroxybutene-2 and water in the presence of a non-volatile liquid acid catalyst and recovering the cyclic ether from the reaction product by distillation, which process comprises the steps of:
    (a) effecting the reaction at a temperature from 110° C. to 180° C. in a plurality of reaction zones connected in series,
    (b) supplying the liquid acetic ester to the first reaction zone, while supplying water to the last reaction zone,
    (c) recycling the gaseous mixture of cyclic ether, water and acetic acid discharged from each of the zones to the preceding reaction zone, while supplying a liquid fraction containing unreacted raw material acetic ester of each of the zones to the succeeding reaction zone, and intimately contacting the gaseous mixture and the liquid fraction in each reaction zone,
    (d) removing the liquid fraction from the last reaction zone,
    (e) supplying the gaseous mixture of cyclic ether water and acetic acid discharged from the first reaction zone to a distillation column,
    (f) recycling the gaseous mixture of cyclic ether and water discharged from the distillation column to a predetermined reaction zone,
    (g) removing the bottom residue containing cyclic ether substantially free from water discharged from the distillation column, and
    (h) recovering the cyclic ether from the bottom residue by distillation.

2. The process for producing a cyclic ether according to claim 1 wherein said reaction is conducted at a pressure of from atmospheric to 3 Kg/cm$^2$G.

3. The process for producing a cyclic ether according to claim 1 wherein said catalyst is supplied to the first reaction zone.

4. A process for producing a cyclic ether according to claim 1, wherein the number of said reaction zones is from two to four.

5. A process for producing a cyclic ether according to claim 1, wherein said catalyst is an inorganic acid selected from the group consisting of sulfuric acid and phosphoric acid.

6. A process for producing a cyclic ether according to claim 1, wherein said catalyst is an organic sulfonic acid selected from the group consisting of benzenesulfonic acid, toluenesulfonic acid and trifluoromethanesulfonic acid.

7. A process for producing a cyclic ether according to claim 1, wherein the gaseous mixture of cyclic ether and water in step (f) is recycled to the first reaction zone.

8. A process for producing a cyclic ether according to claim 1, wherein said raw material acetic ester is 1,4-diacetoxybutane and said product cyclic ether is tetrahydrofuran.

9. A process for producing a cyclic ether according to claim 1, wherein said liquid acid catalyst is used in an amount of from 0.01 to 100 parts by weight on the basis of the raw material acetic ester.

10. A process for producing a cyclic ether according to claim 1, wherein said water employed in step (b) is steam.

11. A process for producing a cyclic ether according to claim 1, wherein the gaseous mixture of cyclic ether, water and acetic acid discharged from the first reaction zone in step (e) is subjected to distillation to separate liquid acetic acid as a bottom residue and a gaseous mixture of cyclic ether and water as a top fraction, the latter being supplied to the distillation column, and, in step (g), a bottom residue containing cyclic ether substantially free from water and acetic acid is recovered.

12. A process for producing a cyclic ether by reacting an acetic ester of 1,4-butanediol or 1,4-dihydroxybutene-2 and water in the presence of a non-volatile liquid acid catalyst and recovering the cyclic ether from the reaction product by distillation, which process comprises the steps of:
 (a) effecting the reaction at a temperature from 110° C. to 180° C. in two continuous reaction zones,
 (b) supplying the raw material liquid acetic ester to the first reaction zone, while supplying water to the second zone,
 (c) supplying the liquid fraction discharged from the first reaction zone to the second zone, while recycling the gaseous mixture of cyclic ether, water and acetic acid discharged from the second zone to the first reaction zone,
 (d) removing the liquid fraction discharged from the second reaction zone,
 (e) supplying the gaseous mixture of cyclic ether, water and acetic acid discharged from the first reaction zone to a distillation column,
 (f) recycling the gaseous mixture of cyclic ether and water discharged from the distillation column to the first reaction zone,
 (g) removing the bottom residue containing cyclic ether substantially free from water from the distillation column, and
 (h) recovering the cyclic ether from the bottom residue by distillation.

13. A process for producing a cyclic ether according to claim 12, wherein the gaseous mixture of cyclic ether, water and acetic acid discharged from the first reaction zone in step (e) is subjected to distillation to separate liquid acetic acid as a bottom residue and a gaseous mixture of cyclic ether and water as a top fraction, the latter being supplied to the distillation column, and, in step (g), a bottom residue containing the cyclic ether substantially free from water and acetic acid is recovered.

* * * * *